United States Patent [19]
Elist

[11] Patent Number: 5,899,849
[45] Date of Patent: May 4, 1999

[54] SUBCUTANEOUS PENILE IMPLANT

[76] Inventor: James Elist, 620 N. Camden Dr., Beverly Hills, Calif. 90210

[21] Appl. No.: 08/934,860

[22] Filed: Sep. 22, 1997

[51] Int. Cl.$^6$ ........................................................ A61F 5/00
[52] U.S. Cl. .............................. 600/40; 600/38; 128/898; 623/11
[58] Field of Search .................................... 128/898, 897; 600/38, 40; 623/11–12

[56] References Cited

U.S. PATENT DOCUMENTS

| | | | |
|---|---|---|---|
| 3,893,456 | 7/1975 | Small et al. | 600/40 |
| 4,201,202 | 5/1980 | Finney et al. | 600/40 |
| 4,566,446 | 1/1986 | Fogarty | 600/40 |
| 5,063,914 | 11/1991 | Cowen | 600/40 |
| 5,611,515 | 3/1997 | Benderev et al. | 128/898 |

*Primary Examiner*—Cary E. O'Connor
*Assistant Examiner*—Michael Astorino
*Attorney, Agent, or Firm*—Gene Scott-Patent Law & Venture Group

[57] ABSTRACT

The present invention is a penile prosthesis device and a method for surgical installation. The prosthesis device is designed to be subcutaneously implanted into a penis above the corpus cavemosum and extending from the base of the penis to the glans penis. The prosthesis device contains one or more inflatable tubular sacks for enabling an erectile function of the penis, and these are covered by a shaped body for enabling an improved appearance, texture and size to the penis. Integral with the tubular sack is a base which is sutured to the pubic bone. The invention includes a manual pump preferably implanted into the scrotum and interconnected with the base means by a tube, used to inflate the tubular sacks. A fluid is pumped by the pump through the tube, through the base, and into the inflatable tubular sacks for pressurization thereof so as to cause the tubular sacks to achieve rigidity, thereby causing the penis to become erect. If the pump is not large enough to contain enough fluid to inflate the inflatable tubular sack, the invention includes a reservoir that feeds into the pump.

7 Claims, 4 Drawing Sheets

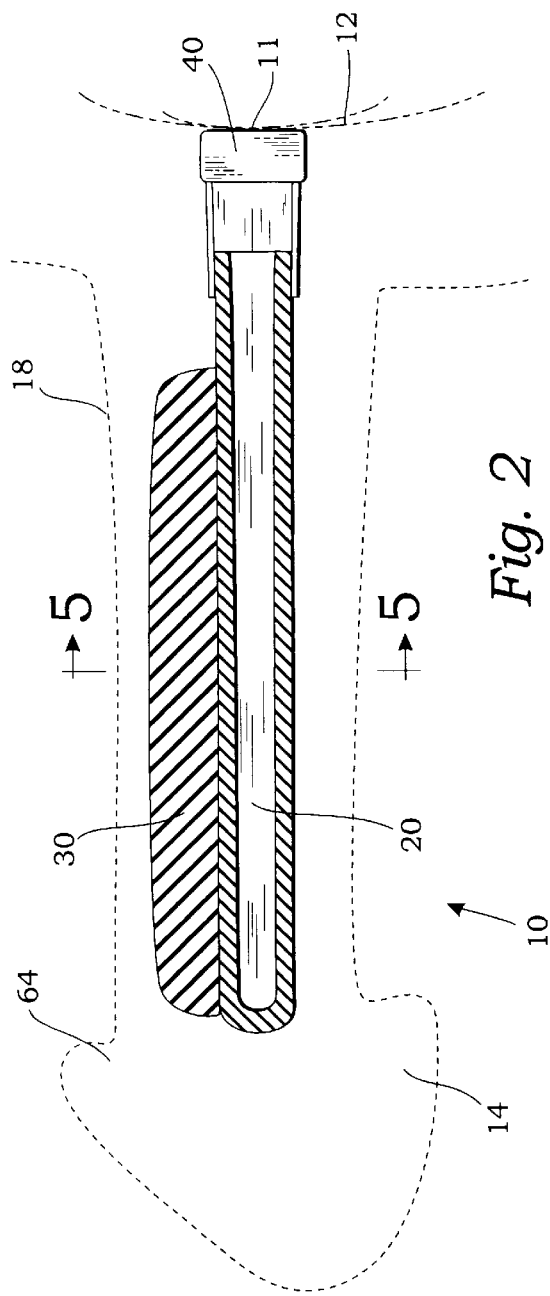
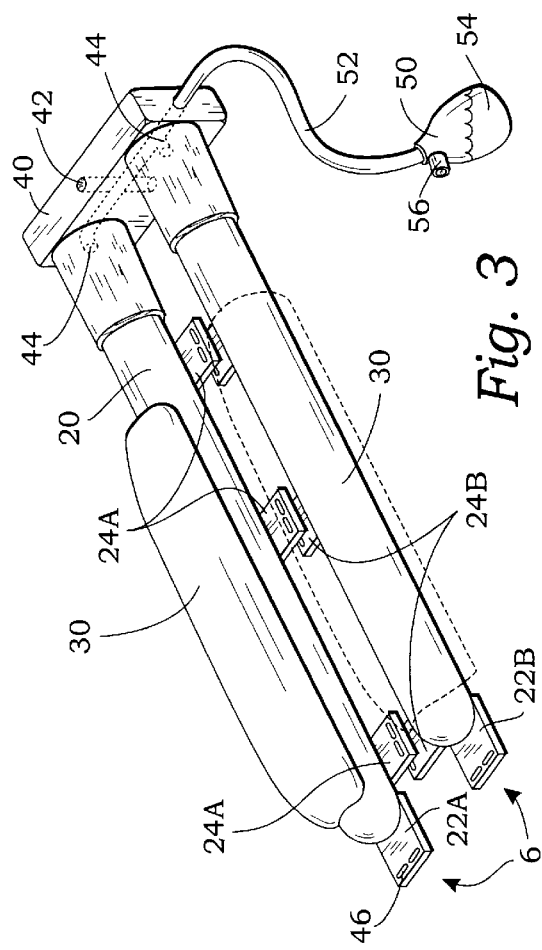

SUBCUTANEOUS PENILE IMPLANT

BACKGROUND OF THE INVENTION

1. Field of the Invention

This invention relates generally to a penile prosthesis for improved function and appearance, and more particularly to a penile implant for subcutaneous operation and a surgical implantation method therefor.

2. Description of the Related Art

The following art defines the present state of this field:

Finney, U.S. Pat. No. 4,204,530 discloses an implantable sleeve for increasing the penile diameter. The sleeve includes a flexible sheet of soft, physiologically acceptable implantable material, the sheet being of sufficient length when formed in the general shape of a cylindrical sleeve to extend from the glans penis to the base of the penis, and of a width which is insufficient to completely encircle the penis, but sufficient to cover the corpora cavernosa. The sheet preferably has edges which are rounded and tapered side edges. The sleeve also includes suturing strips on the inside wall of the sleeve, adjacent the side edges of the sheet, which facilitate the suturing of the sheet to the tunica albuginea. The sleeve further includes porous patches located on the interior of the inside wall of the sleeve into which fibroblasts from the underlying tissues can grow to further anchor the sleeve to the tunica albuginea. In the preferred embodiment, the sheet is of very soft, medical grade silicone elastomer, and suturing strips are of Dacron (tm) fabric and the porous patches are of Dacron(tm) fabric or fluff.

Yamanaka, U.S. Pat. No. 4,235,227 teaches an artificial corpus cavernosum device which is designed to be implanted into the impaired penis of a patient for the remedy of his impotence. The device is at least one artificial corpus cavemosum penis which comprises an elongated tubular pouch made of an artificial thin membrane to be implanted into the penis and for selectively receiving and being filled with a fluid for erecting the penis. The invention includes a container made of an artificial thin membrane for storing the fluid under the normal condition when the penis is not inflated. This container is implantable into the scrotum and is connected to the tubular pouch with a slenderized conduit means for connecting at least one artificial corpus cavemosum penis to the container means in fluid communication with one another. The tube has a check valve interposed in fluid communication with the container means, and having a valve member provided with a through-hole(s) for allowing the fluid, once forcibly delivered from the container means, to pass to the artificial corpus cavernosum penis and to return to the container means again little by little through the through-hole(s).

Rogers, U.S. Pat. No. 4,281,648 discloses an inflatable condom, prophylactic or prosthetic device having conventional anterior portion and retaining ring or reinforced edge with an expandable secondary portion extending from the anterior member, and having an air duct extending inside the anterior portion in communication with the secondary portion to facilitate controlled inflation of the secondary portion responsive to manipulation of a pressure bulb.

Trick, U.S. Pat. No. 4,369,771 discloses a simple, reliable pressure control valve for a medical device having a hydraulic system. The system is comprised of a valve housing having an open top and a bottom and an inwardly directed shoulder partially closing the top; a poppet with an upwardly extending stem mounted in the housing between the top and the bottom; a sealing edge mounted on the poppet circumferentially about the stem, and a calibrated spring urging the poppet towards the open top of the housing so that the sealing edge is in sealing contact with the underside of the shoulder and the stem extends above the top of the housing so that manual pressure can be exerted upon the stem to open the valve, or the valve can be opened by a hydraulic pressure which exerts sufficient force upon the top of the poppet to overcome the force of the spring.

Schroeder, U.S. Pat. No. 4,407,275 discloses a semi-rigid annular ring having individual expandable chambers on the internal wall that are distended separately by fluid pressure. A multi-port flexible conduit is connected to the ring, having individual ports for each chamber. Fluid pressure is supplied through the conduit manually by a bulb, or electrically by a pump through a circular valve plate allowing the chambers to expand and contract in linear sequence. When a penis is placed into the ring and fluid pressure is applied, blood is forced to the end of the organ through the successive expansion and contraction of the bellows in wave fashion mechanically creating an erect condition of the organ.

Yachia et al., U.S. Pat. No. 4,523,584 discloses a penile erectile system for treating male impotency. The system comprises a sleeve of biocompatible material having at least one pressurizable chamber which is adapted to be implanted about the penile shaft of a patient. A fluid reservoir of pressurizing fluid, and a pump for transferring the fluid under pressure from the reservoir to the chamber is placed beneath the penile skin, between the skin and the shaft. The system also includes tubing connecting the reservoir and pump to the pressurizable chamber, and a valve for controlling the flow of fluid into, and out of, the pressurizable chamber. In a preferred embodiment, a pressure bulb. serves both as the fluid reservoir and the pump.

Fischell, U.S. Pat. No. 4,628,912 describes a penile erection prosthesis that has a bellow-like adjustable root or tip extender that can be elongated or shortened by adding or deleting fluid from an internal chamber of the extender. By continuously adjusting the amount of fluid added or deleted, the length of the extender can be continuously adjusted. This adjustment can be made either during surgical implant or post-operatively by penetrating the skin with a non-coring needle and entering the extender to add or delete fluid. The length of the implant can be adjusted by adding or deleting fluid either from the root extender or from the tip end extender.

Whitehead, U.S. Pat. No. 4,665,903 teaches a prosthetic device for implantation within the penis which has a pumping mechanism that is integral with, and is in fluid communication with two fluid storage sections. Fluid is pumped manually from the proximal storage section to distal storage section and then to four distal expansile sections that inflate to render the penis rigid and capable of sexual activity. Undesirable shrinkage of the erect penis is avoided through a rigid frame and bellows that prevent the proximal reservoir from contracting longitudinally and radially as fluid is withdrawn from this storage section to produce the erect penis.

Trick et al., U.S. Pat. No. 4,726,360 discloses a penile prosthesis which is adapted to be surgically implanted in man for the treatment of erectile impotence. The prosthesis includes at least one elongated, flexible cylindrical member which is adapted to be implanted into the corpus cavernosum of the pendulous penis, a pressure bulb for pressurizing liquid, and tubing connecting the member and the bulb. The member includes an inner non-distensible pressure chamber and an outer distensible chamber. The two chambers are connected by a passage and a valve for controlling flow through the passage so that fluid can be transferred from the pressure bulb, via the pressure chamber, to the outer chamber to cause it to distend, and in turn increase penile girth.

Daly, U.S. Pat. No. 4,773,403 describes and improved penile prosthesis to be surgically implanted in man for the treatment or erectile impotence and includes at least one elongated, flexible cylinder containing therein a hydraulic system comprising a pressure chamber, a reservoir and a pump. It also includes an outer girth-adjusting chamber concentric with the pressure bulb located outside the cylinder so that the girth-adjusting chamber can be inflated and the girth of a penis increased by transferring fluid from the pressure bulb to the adjusting chamber.

Trick, U.S. Pat. No. 4,917,110 discloses an implantable prosthesis for correcting erectile impotence. The prosthesis includes at least one penile implant with a pressure chamber, an accumulator charged with fluid, tubing connected the accumulator to the pressure chamber of the implant, a valve which is normally closed, and a lever which can be moved to open the valve so that pressurizing fluid will flow from the accumulator into the pressure chamber.

Lue et al., U.S. Pat. No. 4,982,731 teaches a method and system for augmenting penile erection in a human male. An inflatable cuff is placed circumferentially around the corpora carvernosa, the deep dorsal vein, and the cavernous veins, adjacent to the hilum of the penis. Selective compression of the cuff will function to restrict venous drainage to augment penile erection. The cuff is adapted to have opposite ends thereof attached together and at least one inflatable vesicle is formed on the inner side of the cuff. A pump, including an attendant control system, is sized for implantation in a scrotum whereby the pump can be selectively squeezed to inflate and fluid pressurize the vesicle to compress the cuff around the penis. A control circuit, connected between the cuff and the pump, functions to automatically deflate the cuff after a predetermined period of time has elapsed.

Zinner et al., U.S. Pat. No. 5,069,201 teaches a penile prosthesis which includes proximal and distal end portions with an intermediate normally flexible, nondistensible, collapsible main body portion that adjoins the proximal and distal portions. The main body portion includes filler elements that, in some embodiments of the invention, limit radial expansion of a rigidification chamber of the main body portion, and in other embodiments, limit radial constriction of the rigidification chamber. In some embodiments of the invention, rigidification is accomplished by movement of fluid into a rigidification chamber and in other embodiments of the invention rigidification is accomplished by movement of fluid out of a rigidification chamber. The prosthesis includes a manually maniputable pumping arrangement to establish the necessary fluid movement for development of an erectile condition or a flaccid condition as desired.

Trick, U.S. Pat. No. 5,101,813 discloses a sterile, fully assembled, multi-component, penile erectile system which is to be surgically implanted in man for the treatment of erectile impotence. The system includes at least one elongated, flexible cylindrical member with a pressure chamber for implanting into the pendulous penis; a pressure bulb to be implanted in the scrotal sac; tubing integrally connecting the pressure chamber and the bulb to form a closed system; and, a system for adding or subtracting fluid from the system. The tubing is reinforced so that it will not collapse under suction or kink when bent. In one embodiment the pressure bulb is a multi-stroke pump and in another embodiment there is a receptacle for storing any tubing in excess of that required to extend between two or more components in a given patient. A method of sterilizing and packaging the system so that it can be provided to a surgeon assembled, filled and sterile is also described.

Elist, U.S. Pat. No. 5,445,594 teaches an implant device for expanding the girth and length of a penis. A soft, flexible body is implanted between the shaft and the skin of the penis. The body takes the shape of a partial cylindrical sleeve that has an outer, relatively elastic sheet member and an inner, relatively inelastic sheet member. When implanted, the body covers the corpus cavernosum of the penis and does not or only partially covers the urethra, and extends in length between the glans penis and the base of the penis. A principally closed sack is formed between the inner and outer sheet members for receiving a fluid under pressure from a fluid source. Spring-like ribs are embedded within the inner sheet member for preventing collapse of the inner sheet member when the body is deflated.

The prior art teaches devices which can be implanted to replace a damaged corpus cavernosum. The prior art also teaches devices to treat impotency, as well as sheaths which can be fitted around a penis to augment size. However, the prior art does not teach a prosthesis which can be implanted to increase the length and girth of the penis while maintaining a smooth, natural look and feel, both while flaccid and while inflated. The present invention fulfills these needs and provides further related advantages as described in the following summary.

SUMMARY OF THE INVENTION

The present invention teaches certain benefits in construction and use which give rise to the objectives described below.

The present invention provides a penile prosthesis device designed to be subcutaneously implanted into a penis adjacent to a pubic bone and extending to the base of the glans penis. The device is an inflatable tubular sack means for enabling an erectile function of the penis covered by a shaped body means for enabling an improved appearance, texture and size to the penis. Integral with the tubular sack means is a base means for mounting the device to the pubic bone. The invention also includes a pump means preferably implanted into the scrotum and interconnected with the base means with a tube, used to inflate the tubular sack means. A fluid is pumped by the pump means through the tube, through the base, and into the inflatable tubular sack means for pressurization thereof so as to cause the tubular sack means to achieve rigidity, thereby causing the penis to become erect. If the pump is not large enough to contain enough fluid to inflate the inflatable tubular sack, the invention includes a reservoir means that feeds into the pump means.

The invention also includes the surgical procedure by which the above-described invention is implanted into a patient under general anesthesia. A pair of integral shaped body means and tubular sack means is inserted between the penile skin and the bucks facia along the top half of the penis through an incision into the penis. A plurality of lateral tabs extending from one of the pair of integral shaped body means and tubular sack means is then joined to the corresponding lateral tabs extending from the other of the pair of integral shaped body means and tubular sack means. The base of the device is sutured to the periosteum of the pubic bone. The pump means is then inserted into a scrotal sack of the patient and connected to the base with a tube, and the incisions are closed.

A primary objective of the present invention is to provide an erection enhansing prosthesis which can be implanted subcutaneously in the penis and is therefore later removable should complications arise, i.e., a reversible procedure.

A further objective is to increase the length and girth of the penis without causing structural damage to the penis.

Another objective is to provide a prosthesis capable of maintaining a smooth, natural look and feel, both while flaccid and while inflated.

A further objective is to teach a method of surgically implanting the prosthesis to maximize its effectiveness while minimizing any complications or adverse side effects.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 2 is a side schematic view thereof showing the penis in the erect state;

FIG. 3 is a perspective view thereof showing a portion in phantom line so as to view details of the invention normally obscured from view;

DETAILED DESCRIPTION OF THE INVENTION

Figure 5:
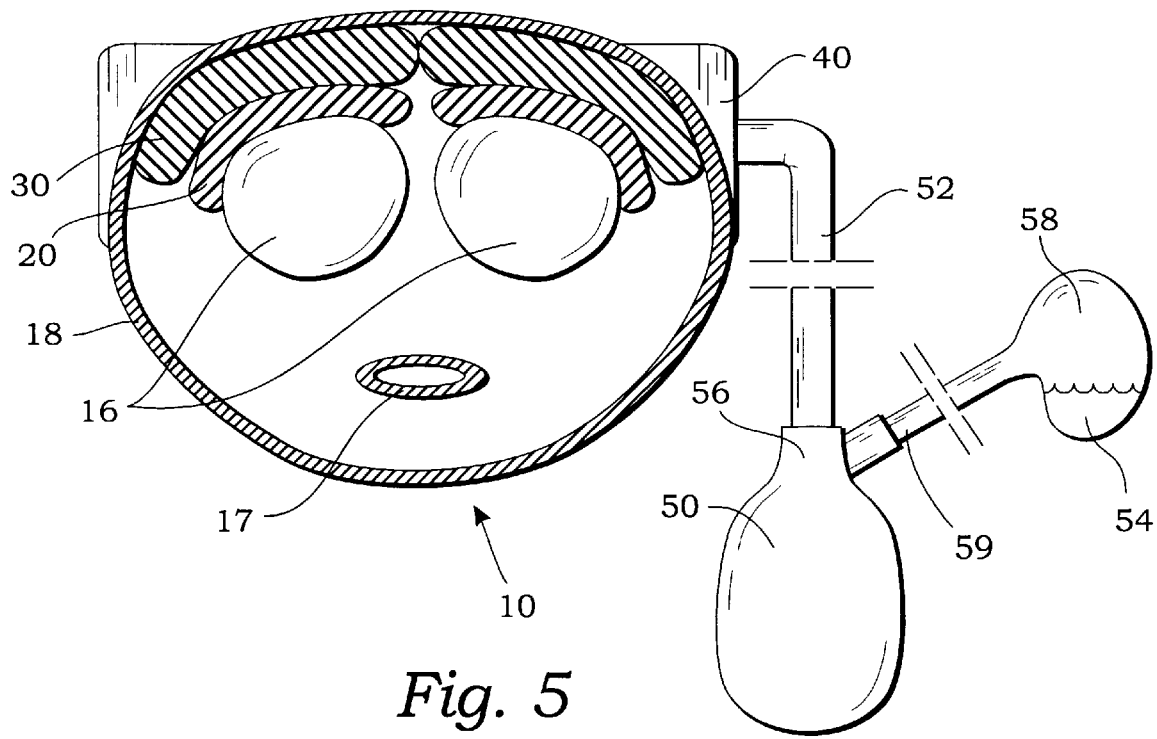
FIG. 5 is a section view taken along cutting line 5—5 in FIG. 2 and particularly showing the preferred cross-sectional contour of the shaped body means of the invention and its preferred location within the penis, a base means of the invention being shown out of position in the background of this figure for orientation purposes.

The above described drawing figures illustrate the invention, a penile prosthesis device 5 designed to be subcutaneously implanted into a penis 10, anchored to the periosteum 11 of the patient's pubic bone 12 and extending to the base of the glans penis 14. The prosthesis device 5 fits above the corpus cavernosum 16 (see FIG. 5) opposite the corpus spongiosum 17 and under the skin 18 which covers the penis.

Figure 8:
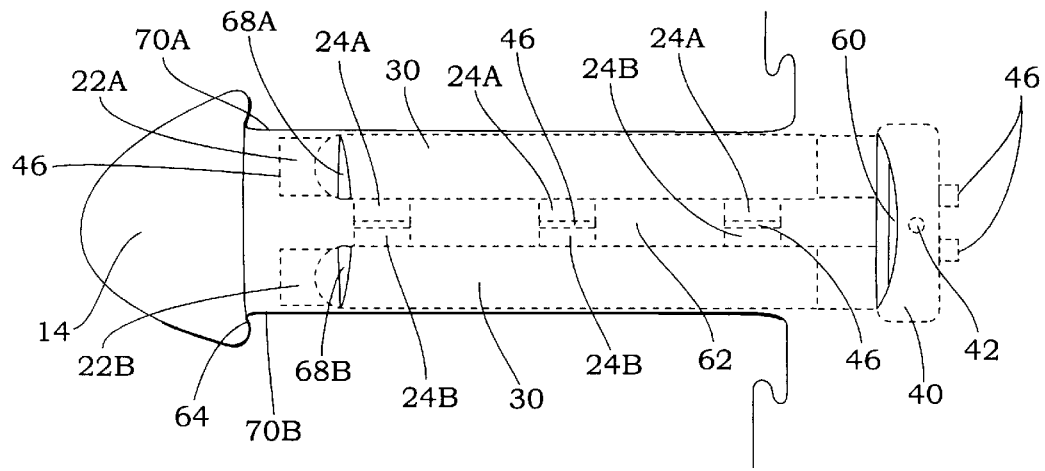
FIG. 8 is a top plan view of a penis showing the incisions used to install the invention and particularly showing the position of the attachment tabs of the invention.

The prosthesis device 5 has at least one, but preferably two or more, inflation assemblies 6 each comprising an inflatable tubular sack means 20 for enabling an erectile function of the penis 10 covered by a shaped body means 30 for enabling an improved appearance, texture and size to the penis 5. The inflatable tubular sack means 20 must be made of a flexible bio-compatible material and is preferably made of DACRON(TM) mesh manufactured by DuPont. It is preferably 0.005 –0.015 inches thick. As shown in FIG. 3, attached to either the inflatable tubular sack means 20 or shaped body means 30 is at least one front tab 22 and at least one, preferably a plurality of lateral tabs 24. The tabs referenced by numerals 22 and 24 are also shown as 2A and 22B, and 24A and 243B, respectively, where the letter suffix denotes the left and right side locations of the tabs. As shown in FIG. 8, when the prosthesis device 5 is surgically implanted, as described in more detail below, these tabs 22 and 24 are used to secure the prosthesis device 5 into its proper position. These tabs 22 and 24 are also preferably made of DACRON(TM) mesh. The inflatable tubular sack means 20 can be empty, but preferably contains porous silicone or foam silicone or another material which will provide body while allowing fluid to enter and leave the tubular sack means without being obstructed.

Figure 6:
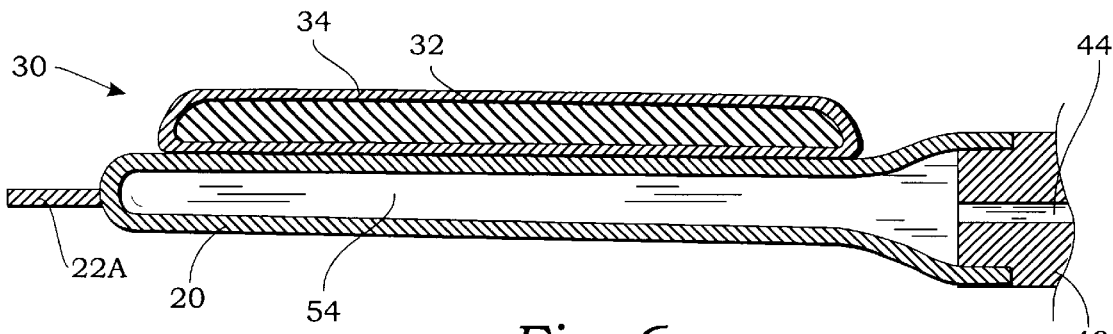
FIG. 6 is a longitudinal section of the invention showing a first embodiment of the invention wherein the shaped body means is a foam-like material inserted into a closed sack.
Figure 7:
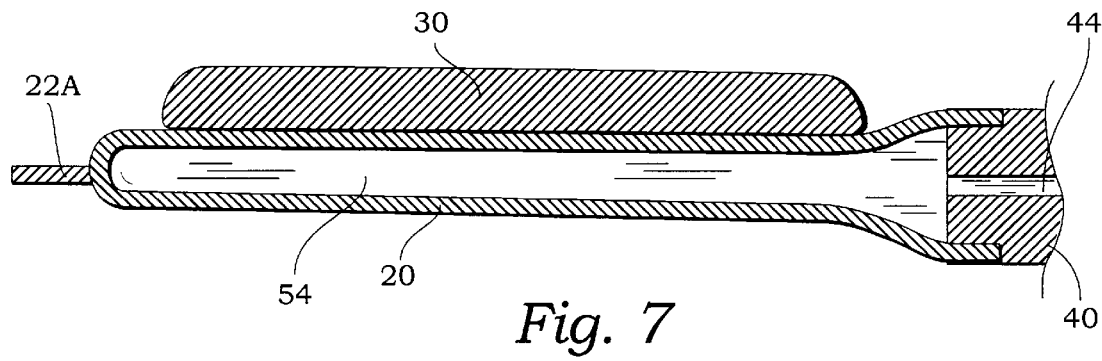
FIG. 7 is a longitudinal section of the invention showing a second embodiment of the invention wherein the shaped body means is a foam-like material used directly without the closed sack.

The shaped body means 30 is preferably made of a plurality of sheets 32 encased in a sheet sack 34. This preferred embodiment is shown in FIG. 6. The sheets 32 must provide a look and feel similar to human flesh such as porous silicone or foam silicone, or some other foam or rubber with similar properties. The preferred material is polyvinyl acetal (PVA). This shaped body means 30 not only conceals the tubular sack means 20, it also increases the girth of the penis 10. The hardness of this material is preferably 15 on the Durometer scale, Shore A. The total thickness of all of the sheets 32 is preferably ¼ to ½ inches. The length of the sheets 32 varies according to the desired length of the penis 10. Breaking the shaped body means 30 into many layers creates a more realistic texture and also allows the easier flexing of the penis 10 between the erect and flaccid positions because this configuration allows the sheets 32 to slide across each other for greater flexibility. These sheets 32 are surrounded by a sheet sack 34. This sheet sack 34 must be bio-compatible and smooth to minimize tissue adhesion. This also simulates the natural feel of the penis 10 and allows the natural expansion and contraction of the penis 10. The preferred material is silicone sheet such as that manufactured by Bentec Medical in Sacramento, California. The sheet sack 34 is heat bonded or otherwise attached to the inflated tubular sack 20. In an alternative embodiment, as shown in FIG. 7, the sheet sack is not used and the shaped body means 30 is made of a monolithic and shaped body of a bio-compatible rubber or foam as described above such as porous silicone in a solid silicone shell. This shaped body means 30 is attached to the top of the inflatable tubular sack means 20 preferably by heat welding or thermal bonding.

Integral with the tubular sack means 20 is a base means 40 preferably made of molded silicone. The base means 40 preferably includes a suture hole 42 and a fluid conduit 44. A suture 46 is passed through the suture hole 42 and into the periosteum 11 of the pubic bone 12, mounting the device to the pubic bone 12. In its preferred embodiment, as shown in FIG. 3, the prosthesis device 5 includes a pair of tubular sack means 20, each with its accompanying shaped body means 30. As shown in FIG. 3, these two tubular sack means 20 are both integrally connected to the base means 40 and in fluid communication with the fluid conduit 44. As shown in FIG. 3, the side tabs 24 from each of the tubular sack means 20 align so they can be sutured together during the installation procedure, as described below.

Figure 1:
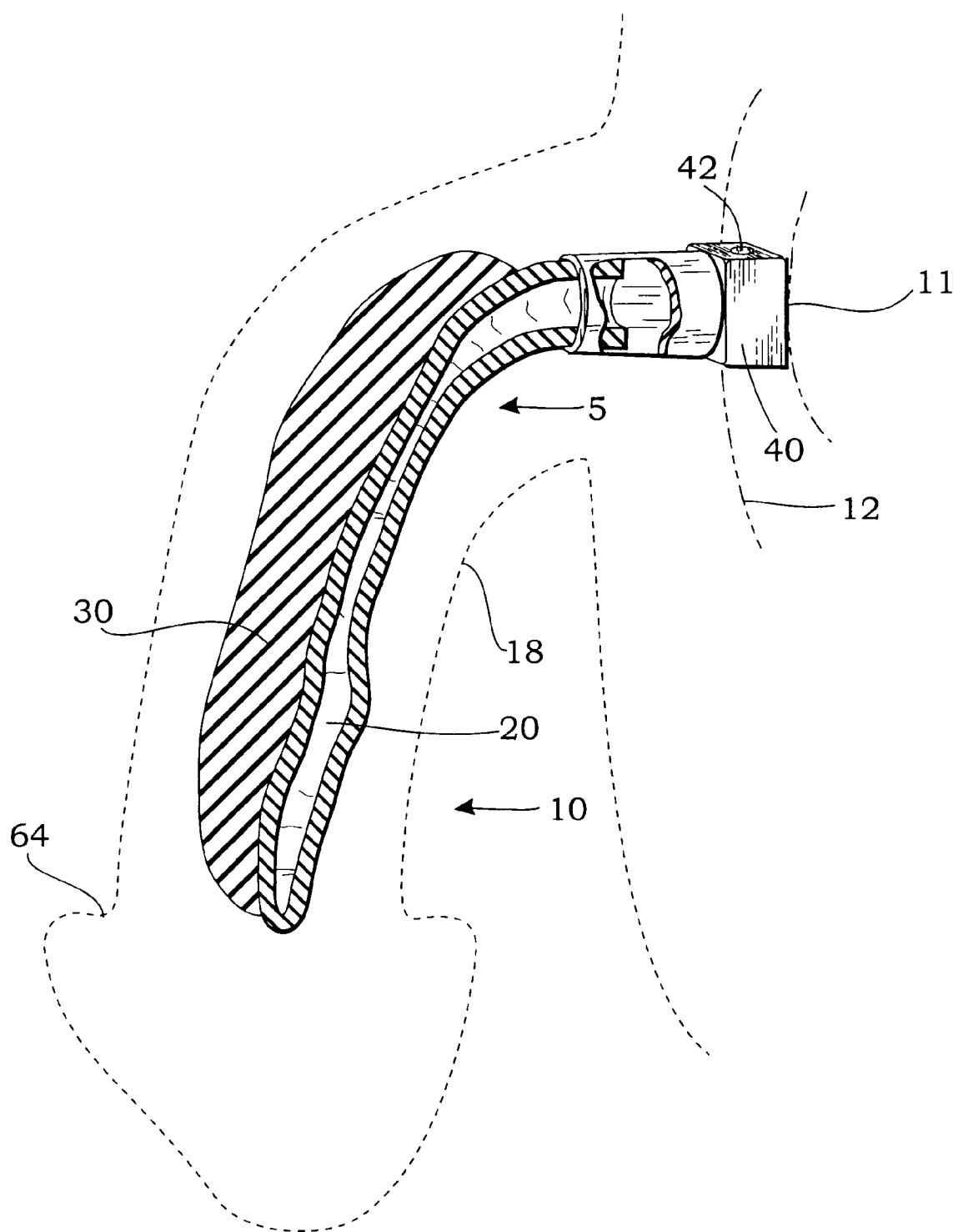
FIG. 1 is a side schematic view of the preferred embodiment of the present invention showing the penis in the flaccid state.
Figure 4:
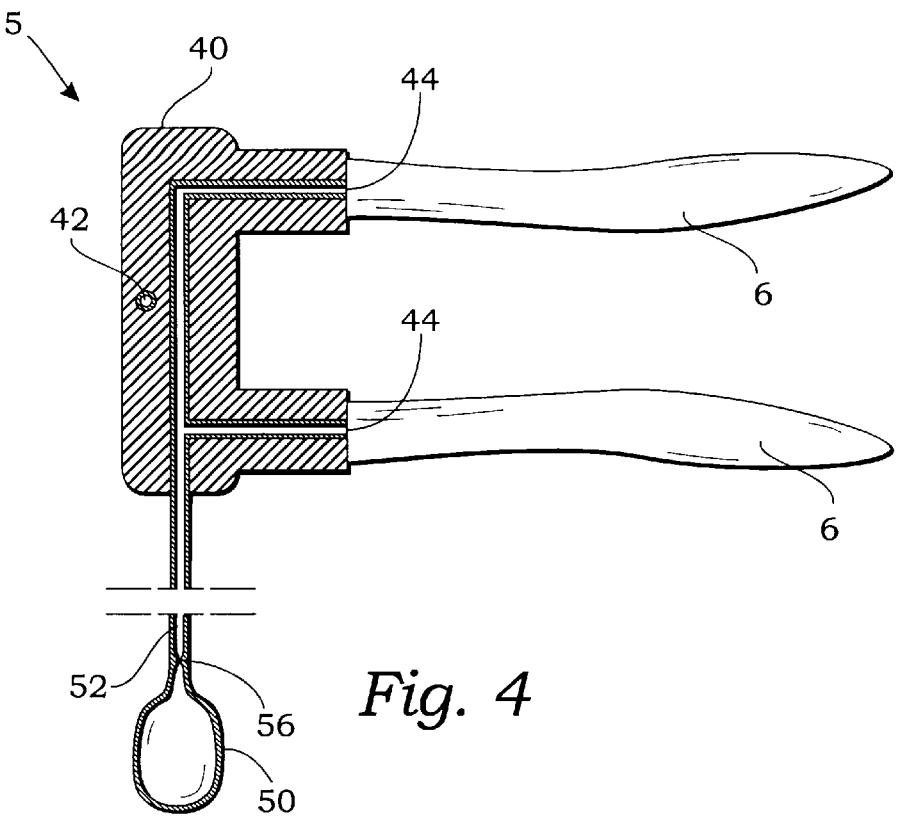
FIG. 4 is a schematic diagram thereof illustrating the means for fluid transfer in the invention.

The prosthesis device 5 also includes a pump means 50 preferably implanted into the scrotum (not shown) and interconnected with the fluid conduit 44 of the base means 40 with a tube 52. The pump means 50 is shown schematically in FIGS. 4 & 5. The tube 52 is preferably made of reinforced extruded silicone tube stock and must be capable of being both bio-compatible, soft and flexible, yet also capable of withstanding the stress of pressurization. A fluid 54, preferably a nontoxic substance such as saline solution, is pumped by the pump means 50 through the tube 52, through the fluid conduit 44 of the base means 40 and into the inflatable tubular sack means 20 for pressurization thereof so as to cause the tubular sack means 20 to achieve rigidity. When in use, this causes the penis 10 to go from its flaccid state shown in FIG. 1, to an erect state shown in FIG. 2. Pressurizing the fluid 54 also serves to increase the diameter of the penis 10. The pump means 50 must contain a valve means 56 which first allows the fluid 54 to be pumped into the inflatable tubular sack means 20 to achieve the required pressurization, yet also can be reversed to allow the fluid 54 to drain back into the pump means 50, thereby deflating the inflatable tubular sack means 20. Such valve means 56 are well known in the art. If the pump means 50 is not large enough to contain enough fluid 54 to inflate the inflatable tubular sack 20, the invention includes a reservoir means 58 in fluid communication with the pump means 50 to supply the pump means 50 with an additional supply of fluid 54. The reservoir means 58 is preferably located in the abdomen not shown) and in fluid communication with the pump means 50 through a reservoir tube 59.

The invention also teaches the implant surgical procedure by which the above-described invention is implanted into a patient (not shown) under general anesthesia. This procedure is designed to utilize the penile prosthesis device 5 in its preferred form, having a pair of inflation assemblies 6 as shown in FIG. 3. As shown in FIG. 8, the first step is to cut an approximately 2 inch long suprapubic incision 60 in the skin of the penis 10 extending from left to right in the suprapubic area of the patient, as shown in FIG. 8. Through this suprapubic incision 60, the penis suspensory ligaments (not shown) are released. A longitudinally directed space 62 is then opened between the penile skin 18 and the bucks facia (not shown) along the top half of the penis 10 extending from the suprapubic incision 60 to the corona 64 of the glans penis 14. An approximately one-half inch long first circumferential incision 68A is cut through the skin 18 approximately one-half half inch from the corona 64 on the top-left side of the penis 10. This procedure is repeated to form a second circumferential incision 68B on the right side of the penis 10. Once the proper incisions have been made, the two inflation assemblies 6 of the penile prosthesis device 5 are inserted through the suprapubic incision 60 and into the longitudinally directed space 62 until the pair of tip tabs 22A and 22B of the invention are adjacent to the circumferential incisions 68A and 68B respectively. The skin 18 adjacent to the corona 64 is elevated at the circumferential incisions 68A and 68B to form flaps of elevated skin 70A and 70B. The tip tabs 22A and 22B are sutured to the bucks fascia (not shown) below the elevated skin 70A and 70B. This elevated skin 70A and 70B is then sutured to the skin 18 of the penis 10 adjacent thereto, closing the circumferential incisions 68A and 68B.

Once the pair of inflation assemblies 6 have been anchored in the area of the corona 64 of the glans penis 14, they are withdrawn through the suprapubic incision 60. It is then possible to join the plurality of lateral tabs 24A and 24B extending from one of the pair of inflation assemblies 6 to the corresponding lateral tabs extending from the other of the pair of inflation assemblies 6. Once they have been joined, the pair of inflation assemblies 6 are reinserted through the suprapubic incision 60 and the base means 40 of the device is sutured to the periosteum 11 of the pubic bone 12. Once the pair of inflation assemblies 6 are in place and the base means 40 is anchored, the pump means 50 is inserted into a scrotal sack of the patient (not shown) and connected to the base means 40 with the tube 52 having a valve means 56. If needed, the reservoir means 58 and the reservoir tube 59 are also inserted at this point. Finally, the suprapubic incision 60 is closed.

The above procedure is fully reversible in that the prosthesis device may be removed from the penis with no lasting damage to the penis or its adjacent tissues or organs. Instead of two inflatable assemblies, as shown in FIG. 3, the invention may be constructed having three or more such assemblies as the particular patient situation dictates.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A penile prosthesis device, the device being adapted for subcutaneous implanting into a penis adjacent to pubic bone, the device comprising:

a shaped body means for enabling an improved appearance and size to the penis;

an inflatable tubular sack means for enabling an erectile function of the penis;

a unitary and monolithic base means integral with the tubular sack means for mounting the device to the pubic bone;

a pump means interconnected with the base means for interchange of a fluid therebetween;

the shaped body means and the tubular sack means being joined integrally with both adapted to extend from the base means to the glans penis with the shaped body means and the tubular sack means, together, being adapted to be sandwiched between a penile skin covering of the penis and the corpus cavernosum, in a position opposite the corpus spongiosum;

the pump means enabling the fluid to move from the base means into the tubular sack means for pressurization thereof so as to cause the tubular sack means to achieve rigidity, thereby causing the penis to become erect.

2. The device of claim 1 wherein the shaped body means and the tubular sack means comprise a left and a right portions spaced apart and positioned longitudinally along the upper left and the upper right quadrants of the penis respectively.

3. The device of claim 2 further including a plurality of suture tabs extending outwardly from the tubular sack means for anchoring the device to the penis.

4. The device of claim 1 wherein the base means provides an internal channel for conducting the fluid from the pump means to the tubular sack means.

5. The device of claim 1 wherein the shaped body means is comprised of a flexible tube enclosing an insert of a foam-like material, the body means approximating the resilience and feel of the human penis.

6. The device of claim 1 wherein the shaped body means is comprised of a foam-like material approximating the resilience and feel of the human penis.

7. The device of claim 1 further including a reservoir means interconnected with the pump means for interchange of the fluid therebetween.

* * * * *